United States Patent
King et al.

(10) Patent No.: US 10,253,051 B2
(45) Date of Patent: Apr. 9, 2019

(54) PREPARATION OF TITANIUM CATECHOLATE COMPLEXES IN AQUEOUS SOLUTION USING TITANIUM TETRACHLORIDE OR TITANIUM OXYCHLORIDE

(71) Applicant: LOCKHEED MARTIN ADVANCED ENERGY STORAGE, LLC, Bethesda, MD (US)

(72) Inventors: Evan R. King, Quincy, MA (US); Brian D. Pickett, Baltimore, MD (US); Malcolm Goodman, Bel Air, MD (US); Guoyi Fu, Glenwood, MD (US)

(73) Assignees: Lockheed Martin Energy, LLC, Bethesda, MD (US); Cristal USA, Inc., Glen Burnie, MD (US)

( * ) Notice: Subject to any disclaimer, the term of this patent is extended or adjusted under 35 U.S.C. 154(b) by 258 days.

(21) Appl. No.: 15/071,047

(22) Filed: Mar. 15, 2016

(65) Prior Publication Data

US 2016/0272659 A1   Sep. 22, 2016

Related U.S. Application Data

(60) Provisional application No. 62/133,610, filed on Mar. 16, 2015.

(51) Int. Cl.
*C07F 7/28* (2006.01)
*H01M 8/18* (2006.01)

(52) U.S. Cl.
CPC .............. *C07F 7/28* (2013.01); *H01M 8/188* (2013.01); *H01M 2300/0002* (2013.01); *Y02E 60/528* (2013.01)

(58) Field of Classification Search
CPC ........... C07F 7/28; H01M 8/188; H01M 8/20; H01M 8/08

(Continued)

(56) References Cited

U.S. PATENT DOCUMENTS 1,279,295 A    9/1918   Downs
1,988,575 A    1/1935   Schmidt
(Continued)

FOREIGN PATENT DOCUMENTS

CN    1284208 A       2/2001
CN    101877412 A     11/2010
(Continued)

OTHER PUBLICATIONS

Brezina, "Study of the reduction of oxygen on a carbon paste electrode in an alkaline medium," Coll. Czech. Chem. Commun., 1973, 38(10), 3024-3031.

(Continued)

*Primary Examiner* — Sean P Cullen
(74) *Attorney, Agent, or Firm* — Baker & Hostetler LLP

(57) ABSTRACT

Titanium coordination complexes, particularly titanium catecholate complexes, can be attractive active materials for use in flow batteries. However, such coordination complexes can be difficult to prepare from inexpensive starting materials, particularly in aqueous solutions. Titanium oxychloride and titanium tetrachloride represent relatively inexpensive titanium sources that can be used for preparing such coordination complexes. Methods for preparing titanium catecholate complexes can include combining one or more catecholate ligands and titanium oxychloride in an aqueous solution, and reacting the one or more catecholate ligands with the titanium oxychloride in the aqueous solution to form the titanium catecholate complex. Titanium tetrachloride can be used as a precursor for forming the titanium oxychloride in situ. In some instances, the titanium catecholate complex can be isolated in a solid form, which can be substantially free of alkali metal ions.

20 Claims, 3 Drawing Sheets

(58) Field of Classification Search
USPC .............................. 429/101, 105; 568/753
See application file for complete search history.

(56) References Cited

U.S. PATENT DOCUMENTS

| | | | |
|---|---|---|---|
| 2,353,782 A | 7/1944 | Neumark | |
| 2,415,792 A | 2/1947 | Gravell | |
| 3,294,588 A | 12/1966 | Morton | |
| 3,425,796 A | 2/1969 | Bauer | |
| 3,428,654 A | 2/1969 | Rubinfeld | |
| 3,573,984 A | 4/1971 | Shah | |
| 3,707,449 A | 12/1972 | Reinhardt et al. | |
| 3,772,379 A | 11/1973 | Woodgate | |
| 3,801,642 A | 4/1974 | Worrel | |
| 3,876,435 A | 4/1975 | Dollman | |
| 3,916,004 A | 10/1975 | Okada et al. | |
| 3,919,000 A | 11/1975 | Yarrington | |
| 3,920,756 A | 11/1975 | Tahara et al. | |
| 3,929,506 A | 12/1975 | Leddy et al. | |
| 3,985,517 A | 10/1976 | Johnson | |
| 3,985,585 A | 10/1976 | Tuttle et al. | |
| 4,046,861 A | 9/1977 | Reinhardt et al. | |
| 4,064,324 A | 12/1977 | Eustace | |
| 4,069,371 A | 1/1978 | Zito | |
| 4,126,529 A | 11/1978 | DeBerry | |
| 4,180,623 A | 12/1979 | Adams | |
| 4,202,799 A | 5/1980 | Yoshimura et al. | |
| 4,233,144 A | 11/1980 | Pace et al. | |
| 4,362,791 A | 12/1982 | Kaneko et al. | |
| 4,378,995 A | 4/1983 | Gratzfeld et al. | |
| 4,410,606 A | 10/1983 | Loutfy et al. | |
| 4,436,711 A | 3/1984 | Olson | |
| 4,436,712 A | 3/1984 | Olson | |
| 4,436,713 A | 3/1984 | Olson | |
| 4,436,714 A | 3/1984 | Olson | |
| 4,443,423 A | 4/1984 | Olson | |
| 4,443,424 A | 4/1984 | Olson | |
| 4,468,441 A | 8/1984 | D'Agostino et al. | |
| 4,485,154 A | 11/1984 | Remick et al. | |
| 4,520,083 A | 5/1985 | Prater et al. | |
| 4,563,403 A | 1/1986 | Julian | |
| 4,592,973 A | 6/1986 | Pemsler et al. | |
| 4,617,244 A | 10/1986 | Greene | |
| 4,680,308 A | 7/1987 | Schwartz et al. | |
| 4,818,646 A | 4/1989 | Takakubo et al. | |
| 4,880,758 A | 11/1989 | Heistand, II et al. | |
| 4,952,289 A | 8/1990 | Ciccone et al. | |
| 4,959,135 A | 9/1990 | Zenner et al. | |
| 4,973,720 A | 11/1990 | Saito et al. | |
| 5,084,533 A | 1/1992 | Shah et al. | |
| 5,102,906 A | 4/1992 | Nakayama et al. | |
| 5,122,461 A | 6/1992 | Hsiung et al. | |
| 5,264,097 A | 11/1993 | Vaughan | |
| 5,302,481 A | 4/1994 | Ong | |
| 5,318,865 A | 6/1994 | Kaneko et al. | |
| 5,433,934 A | 7/1995 | Chang et al. | |
| 5,472,807 A | 12/1995 | Licht et al. | |
| 5,643,670 A | 7/1997 | Chung | |
| 5,679,239 A | 10/1997 | Blum et al. | |
| 5,759,711 A | 6/1998 | Miyabayashi et al. | |
| 5,785,841 A | 7/1998 | Tseng | |
| 5,876,581 A | 3/1999 | Itaya et al. | |
| 5,910,366 A | 6/1999 | Chowdhury et al. | |
| 6,001,326 A | 12/1999 | Kim et al. | |
| 6,030,517 A | 2/2000 | Lincot et al. | |
| 6,054,230 A | 4/2000 | Kato | |
| 6,461,772 B1 | 10/2002 | Miyake et al. | |
| 6,475,661 B1 | 11/2002 | Pellegri et al. | |
| 6,485,868 B1 | 11/2002 | Tsujioka et al. | |
| 6,555,989 B1 | 4/2003 | Pearson | |
| 6,585,951 B1 | 7/2003 | Hong et al. | |
| 6,624,328 B1 | 9/2003 | Guerra | |
| 7,046,418 B2 | 5/2006 | Lin et al. | |
| 7,193,764 B2 | 3/2007 | Lin et al. | |
| 7,223,833 B1 | 5/2007 | Nielsen et al. | |
| 7,252,905 B2 | 8/2007 | Clarke et al. | |
| 7,265,162 B2 | 9/2007 | Yandrasits et al. | |
| 7,348,088 B2 | 3/2008 | Hamrock et al. | |
| 7,463,917 B2 | 12/2008 | Martinez | |
| 7,508,568 B2 | 3/2009 | Lin et al. | |
| 7,550,231 B2 | 6/2009 | Stauffer | |
| 7,557,164 B2 | 7/2009 | Felix et al. | |
| 7,625,663 B2 | 12/2009 | Clarke et al. | |
| 7,645,540 B2 | 1/2010 | Boone et al. | |
| 7,678,728 B2 | 3/2010 | Olson et al. | |
| 7,745,056 B2 | 6/2010 | Lee et al. | |
| 7,767,777 B2 | 8/2010 | Buesing et al. | |
| 7,927,731 B2 | 4/2011 | Sahu | |
| 7,931,981 B2 | 4/2011 | Boone et al. | |
| 7,935,366 B2 | 5/2011 | Pahuja et al. | |
| 7,998,335 B2 | 8/2011 | Feeney et al. | |
| 8,129,554 B2 | 3/2012 | Schwaiger | |
| 8,187,441 B2 | 5/2012 | Evans et al. | |
| 8,445,118 B2 | 5/2013 | Cordonier et al. | |
| 8,492,581 B2 | 7/2013 | Frost et al. | |
| 8,691,413 B2 | 4/2014 | Esswein et al. | |
| 8,753,761 B2 | 6/2014 | Esswein et al. | |
| 9,300,000 B2 | 3/2016 | Jansen et al. | |
| 9,382,274 B2 | 7/2016 | Esswein et al. | |
| 9,409,842 B1 | 8/2016 | Fu et al. | |
| 2002/0177042 A1 | 11/2002 | Amendola | |
| 2003/0068561 A1 | 4/2003 | Okahara et al. | |
| 2003/0143456 A1 | 7/2003 | Kazacos et al. | |
| 2003/0228394 A1 | 12/2003 | Abdel-Monem et al. | |
| 2004/0096746 A1 | 5/2004 | Wietelmann et al. | |
| 2005/0098437 A1 | 5/2005 | Shiepe | |
| 2005/0244707 A1 | 11/2005 | Skyllas-Kazacos et al. | |
| 2006/0047094 A1 | 3/2006 | Cherkasov et al. | |
| 2007/0275291 A1 | 11/2007 | Gu et al. | |
| 2008/0274385 A1 | 11/2008 | Creeth | |
| 2008/0292964 A1 | 11/2008 | Kazacos et al. | |
| 2009/0110998 A1 | 4/2009 | Miyachi et al. | |
| 2009/0130525 A1 | 5/2009 | Miyachi et al. | |
| 2009/0208807 A1 | 8/2009 | Miyachi et al. | |
| 2009/0308752 A1 | 12/2009 | Evans et al. | |
| 2010/0003586 A1 | 1/2010 | Sahu | |
| 2010/0059388 A1 | 3/2010 | Clarke et al. | |
| 2010/0086823 A1 | 4/2010 | Koshino et al. | |
| 2010/0086983 A1 | 4/2010 | Gellett et al. | |
| 2010/0239946 A1 | 9/2010 | Miyachi et al. | |
| 2011/0014532 A1 | 1/2011 | Knuckey et al. | |
| 2011/0136016 A1 | 6/2011 | Huang et al. | |
| 2011/0189549 A1 | 8/2011 | Sun et al. | |
| 2011/0195283 A1 | 8/2011 | Sun et al. | |
| 2011/0200890 A1 | 8/2011 | Kocherginsky | |
| 2011/0223450 A1 | 9/2011 | Horne et al. | |
| 2011/0244277 A1 | 10/2011 | Gordon, II et al. | |
| 2011/0244367 A1 | 10/2011 | Watahiki et al. | |
| 2012/0052347 A1 | 3/2012 | Wilson et al. | |
| 2012/0077095 A1 | 3/2012 | Roumi et al. | |
| 2012/0107661 A1 | 5/2012 | Lee et al. | |
| 2012/0135278 A1 | 5/2012 | Yoshie et al. | |
| 2012/0171541 A1 | 7/2012 | Park et al. | |
| 2012/0183868 A1 | 7/2012 | Toussaint et al. | |
| 2012/0196188 A1 | 8/2012 | Zhang et al. | |
| 2012/0202099 A1 | 8/2012 | Perry et al. | |
| 2012/0208061 A1 | 8/2012 | Sahu et al. | |
| 2012/0244406 A1 | 9/2012 | Xia et al. | |
| 2012/0263990 A1 | 10/2012 | Kim | |
| 2013/0004819 A1 | 1/2013 | Mun et al. | |
| 2013/0157087 A1 | 6/2013 | Pandy et al. | |
| 2013/0252062 A1 | 9/2013 | Wilkins et al. | |
| 2013/0252137 A1 | 9/2013 | Zhang et al. | |
| 2014/0028260 A1 | 1/2014 | Goeltz et al. | |
| 2014/0028261 A1 | 1/2014 | Esswein et al. | |
| 2014/0030572 A1 | 1/2014 | Esswein et al. | |
| 2014/0030573 A1 | 1/2014 | Esswein et al. | |
| 2014/0030631 A1 | 1/2014 | Esswein et al. | |
| 2014/0051002 A1 | 2/2014 | Esswein et al. | |
| 2014/0051003 A1 | 2/2014 | Esswein et al. | |
| 2014/0080035 A1 | 3/2014 | Esswein et al. | |
| 2014/0138576 A1 | 5/2014 | Esswein et al. | |
| 2014/0178735 A1 | 6/2014 | Wang et al. | |
| 2014/0193687 A1 | 7/2014 | Park et al. | |

(56) References Cited

U.S. PATENT DOCUMENTS

| | | | |
|---|---|---|---|
| 2014/0239906 | A1 | 8/2014 | Anderson et al. |
| 2014/0274936 | A1 | 9/2014 | Piccariello et al. |
| 2014/0349177 | A1 | 11/2014 | Chung et al. |
| 2014/0370403 | A1 | 12/2014 | Narayan et al. |
| 2014/0377666 | A1 | 12/2014 | Kodama et al. |
| 2015/0236543 | A1 | 8/2015 | Brushett et al. |
| 2015/0372333 | A1 | 12/2015 | Odom et al. |
| 2016/0066578 | A1 | 3/2016 | Ala'Aldeen et al. |
| 2016/0149251 | A1 | 5/2016 | Reece |
| 2016/0208165 | A1 | 7/2016 | Li et al. |
| 2016/0264603 | A1 | 9/2016 | Esswein et al. |
| 2016/0268623 | A1 | 9/2016 | Esswein et al. |
| 2016/0276693 | A1 | 9/2016 | Goeltz et al. |
| 2016/0276694 | A1 | 9/2016 | Goeltz et al. |
| 2016/0276695 | A1 | 9/2016 | Esswein et al. |
| 2017/0253620 | A1 | 9/2017 | Humbarger et al. |
| 2017/0256811 | A1 | 9/2017 | Humbarger et al. |
| 2017/0271704 | A1 | 9/2017 | Morris-Cohen |
| 2018/0029965 | A1* | 2/2018 | Millard .................. C07C 37/66 |
| 2018/0029966 | A1* | 2/2018 | Millard ................. H01M 8/188 |
| 2018/0105544 | A1* | 4/2018 | Humbarger ............... C07F 7/28 |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-00/56302 A2 | 9/2000 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO-2014/052682 A2 | 4/2014 |
| WO | WO-2015/069439 A1 | 5/2015 |

OTHER PUBLICATIONS

Caulton, "Systematics and Future Projections Concerning Redox-Noninnocent Amide/Imine Ligands," Eur. J. Inorg. Chem., Jan. 2012, 2012(3), 435-443.

Cerofontain et al. "Sulfonation and sulfation on reaction of 1,2-dihydroxybenzene and its methyl ethers in concentrated aqueous sulfuric acid," Recl Trav Chim Pays-Bas, 1988, pp. 325-330, vol. 107.

Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.

Cohen, "The Association of Ferrocyanide Ions With Various Cations," J. Phys. Chem., Aug. 1957, 61(8), 1096-1100.

Davies, "Eiectroceramics from Source Materials via Molecular Intermediates: PbTi03 from Ti02 via [Ti(catecholate)3]2-," J. Am. Ceram. Soc., Aug. 1990, 73(8), 2570-2572.

Fryda, "Wastewater Treatment With Diamond Electrodes," Diamond Materials, Electrochemical Society Proceedings, 2000, 99(32), 473-483.

Gail, "Cyano Compounds, Inorganic" in Ullmann's Encyclopedia of Industrial Chemistry, 2012, 10, 674-710.

Hollandsworth, "Zinc/Ferrocyanide Battery Development Phase IV" Lockheed Missiles and Space Company, Inc., Contractor report, Sandia Contract DE-AC04-76DP00789, May 1985, 278 pages.

Kim, "Novel catalytic effects of Mn304 for all vanadium redox flow batteries," Chem. Commun., Apr. 2012, 48(44), 5455-5457.

Kulesza, "Electrochemical preparation and characterization of hybrid films composed of Prussian blue type metal hexacyanoferrate and conducting polymer," Electrochimica Acta, Aug. 2001, 46(26-27), 4065-4073.

Leung, "Development of a Zinc-Cerium Redox Flow Battery", 2011, 352 pages.

Leung, "An undivided zinc-cerium redox flow battery operating at room temperature (295 K)," Electrochemistry Communications, 2011, vol. 13, pp. 770-773.

Leung, "Ce(III)/Ce(iV) in methanesulfonic acid as the positive half cell of a redox flow battery," Electrochimica Acta, 2011, vol. 56, pp. 2145-2153.

Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.

Leung, "Characterization of a zinc-cerium flow battery," Journal of Power Sources, 2011, vol. 195, pp. 5174-5185.

Modiba, "Electrochemical impedance spectroscopy study of Ce(IV) with aminopolycarboxylate ligands for redox flow batteries applications," Journal of Power Sources, May 2012, vol. 205, 1-9.

Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.

Modiba, "Electrolytes for redox flow battery systems," Dissertation presented for the degree of Doctor of Philosophy Chemistry at the University of Stellenbosch, Department of Chemistry and Polymer Science, Mar. 2010.

Nguyen, "Flow Batteries," The Electrochemical Society Interface, Fall 2010, 19(3), 54-56.

Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.

Raymond, "Coordination isomers of biological iron transport compounds. VI. Models of the enterobactin coordination site. A crystal field effect in the structure of potassium tris( catecholato )chromate( III) and -ferrate( III) sesq u ihyd rates, K3[M( 02C6H4 )3]. 1 . 5H20, M=chromium, iron," J. Am. Chem. Soc., Mar. 1976, 98(7), 1767-1774.

Saito et al. "DPPH radical-scavenging reaction of protocatechuic acid: differnce in reactivity between acids and their esters," Helv Chim Acta, 2006, pp. 1395-1407, vol. 89.

Sever et al, "Visible absorption spectra of metal-catecholate and metal-tironate complexes," Dalton Trans., pp. 1061-1072, 2004.

Sigma-Aldrich Tris(hydroxymethyl)aminomethane, 2015.

Steenken, "One-electron redox potentials of phenols. Hydroxy- and aminophenols and related compounds of biological interest," J. Phys. Chem., Sep. 1982, 86(18), 3661-3667.

Torres-Gomez, "Energy Storage in Hybrid Organic-Inorganic Materials Hexacyanoferrate-Doped Polypyrrole as Cathode in Reversible Lithium Cells," J. of The Electrochemical Society, 2000, 147(7), 2513-2516.

Trant, "Solubility of Sodium Ferrocyanide and Potassium Ferrocyanide in Solutions of NaOH and KOH Mixtures at 25.degree. C.," University of Rochester, The David T. Kearns Center, Xerox Undergraduate Research Fellows Program, Jul. 28, 2011, 1 page.

Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.

Wang, "Determination of iron, titanium, osmium, and aluminum with tiron by reversephase high performance liquid chromatography/electrochemistry," Microchem. J., Jun. 1991, 43(3), 191-197.

Weber, "Redox flow batteries: a review," Journal of Applied Electrochemistry, Oct. 2011, 41(10), 1137-1164.

(56) References Cited

OTHER PUBLICATIONS

Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
Wang et al., "Issues in Freeze Drying of Aqueous Solutions," Chinese Journal of Chemical Engineering, 2012, 20(3), pp. 551-559.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, Issue 3-4.
Dehaen, et al., "A Self-Assembled Complex with a Titanium (IV) Catecholate Core as a Potential Bimodal Contrast Agent," Chem Eur J, 2012, pp. 293-302, vol. 18.
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Bosch et al., "Novel Catalysis of Hydroquinone Autoxidation with Nitrogen Oxides," J. Org. Chem., 1994, pp. 2529-2536, 59.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom *Suillus tridentinus* (Boletales)," Eur. J. Org. Chem., 2008, pp. 816-825.
Mcomie et al. "The Thiele-Winter Acetoxylation of Quinones," Organic Reactions, 1972, pp. 199-277, 19, John Wiley and Sons, Inc., New York.
Spyroudis, "Hydroxyquinones: Synthesis and Reactivity," Molecules, 2000, pp. 1291-1330, 5.
Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.
IUPAC Compendium of Chemical Terminology, "coordinatively unsaturated complex," 1997, http://old.iupac.org/goldbook/C01334.pdf.
Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.
International Search Report and Written Opinion from PCT/US17/14764, dated Apr. 20, 2017.
International Search Report and Written Opinion from PCT/US16/69190, dated May 3, 2017.
International Search Report and Written Opinion from PCT/US2017/022203, dated Jun. 6, 2017.
Ahluwalia et al., Intermediates for Organic Synthesis, Chapter 1, Phenols, Sections 1.21 and 1.23, (2003), I.K. International Pvt. Ltd.
B.A. Borgias, et al., "Synthetic, Sturctural and Physical Studies of Titanium Complexes of Catechol and 3,5-Di-tert-butylcatechol," Inorg. Chem., 1984, pp. 1009-1016, 23.
International Search Report and Written Opinion from PCT/US17/43393, dated Oct. 5, 2017, 7 pages.
Vliet et al., "Hydroxyhydroquinone Triacetate," Organic Synthesys, 1941, Coll vol. 1, p. 317 (1941), vol. 4, p. 35 (1925) 3 pages.
International Search Report and Written Opinion dated Jan. 19, 2017 from International Application No. PCT/US16/58433.
International Search Report and Written Opinion dated Feb. 17, 2017 from International Application No. PCT/US16/65159.
W. Maison, et al., "Effect of Calcination Temperature on Phase Transformation and Particle size of Barium Titanate Fine Powders Synthesized by the Catecholate Process," ScienceAsia, 2001, pp. 239-243, 27.
Ali et al., "Synthesis and Processing Characteristics of $Ba_{0.65}Sr_{0.35}TIO_3$ Powders from Catecholate Precursors," J Am Ceram Soc, 1993, pp. 2321-2326, vol. 76, No. 9.
Devi et al., "pH-metric investigation on Mixed-Ligand Complexs of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.
Xu, "Mechanics of metal-catecholate complexes: The roles of coordination state and metal types," Scientific Reports, Oct. 10, 2013, 3:2914, pp. 1-7.
Soloveichik, "Flow Batteries: Current Status and Trends," 2015, Chem. Rev., 115 (20), pp. 11533-11558.
Davies, "Electroceramics from Source Materials via Molecular Intermediates: $BaTIO_3$ from $TIO_2$ via $[TI(catecholate)_3]^{2-}$," May 1990, J. Am. Ceram. Soc., Aug. 1990, 73(5), 1429-30.
Extended European Search Report from European Patent Application No. 15863021, dated May 17, 2018, 11 pages.
Chi., Y. et al., "Structural characterization of Sr-Ti and Ba-Ti catecholate complexes: single source precursors for $SrTiO3$ and $BaTiO3$ binary oxides" J. Phys and Chem of Solids 62 (2001) 1871-1879.

* cited by examiner

PREPARATION OF TITANIUM CATECHOLATE COMPLEXES IN AQUEOUS SOLUTION USING TITANIUM TETRACHLORIDE OR TITANIUM OXYCHLORIDE

CROSS-REFERENCE TO RELATED APPLICATIONS

The present application claims the benefit of priority under 35 U.S.C. § 119 from U.S. Provisional Patent Application 62/133,610, filed on Mar. 16, 2015 and incorporated herein by reference in its entirety.

STATEMENT REGARDING FEDERALLY SPONSORED RESEARCH OR DEVELOPMENT

Not applicable.

FIELD

The present disclosure generally relates to energy storage and, more specifically, to flow batteries and methods for preparing active materials for flow batteries.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof will synonymously refer to materials that undergo a change in oxidation state during operation of a flow battery or like electrochemical energy storage system (i.e., during charging or discharging). Although flow batteries hold significant promise for large-scale energy storage applications, they have often been plagued by poorer than expected energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination compounds for this purpose. As used herein, the terms "coordination complex," "coordination compound," "metal-ligand complex" and related variants thereof will synonymously refer to a compound having at least one dative bond formed between a metal center and a donor ligand. The metal center can cycle between an oxidized form and a reduced form in an electrolyte solution, where the oxidized and reduced forms represent states of full charge or full discharge depending upon the particular half-cell in which the coordination compound is present.

Due to their favorable electrochemical properties, titanium coordination complexes can be particularly useful for inclusion as at least one of the active materials within in a flow battery, particularly as the active material in contact with a flow battery's negative electrode. Titanium coordination complexes containing at least one catecholate ligand (i.e., titanium catecholate complexes) can be particularly useful for this purpose. From various commercialization standpoints, aqueous production methods for titanium catecholate complexes using low-cost materials can be highly desirable. Conventional routes for preparing titanium catecholate complexes typically involve the use of various reactive titanium (IV) sources, such as titanium oxysulfate, titanium tetrakis(isopropoxide), and titanium tetrachloride. The former two compounds are rather expensive and are not well suited for commercial scale operations as a result. Titanium tetrachloride, in contrast, is relatively inexpensive, but the high water reactivity of this substance has conventionally precluded its utilization as a starting material in aqueous methods for forming titanium coordination complexes. In particular, titanium tetrachloride reacts with water under typical aqueous conditions to form hydrogen chloride and titanium dioxide, the latter of which is not considered to be a suitable precursor for forming titanium coordination complexes.

In view of the foregoing, aqueous methods for forming titanium coordination complexes, particularly titanium catecholate complexes, using low-cost starting materials would be highly desirable in the art. The present disclosure satisfies the foregoing need and provides related advantages as well.

SUMMARY

In some embodiments, the present disclosure provides methods for preparing titanium catecholate complexes. The methods include: combining one or more catecholate ligands and titanium oxychloride in an aqueous solution, and reacting the one or more catecholate ligands with the titanium oxychloride in the aqueous solution to form a titanium catecholate complex.

In other various embodiments, the present disclosure provides compositions containing titanium catecholate complexes that can lack a metal counterion. The compositions include a titanium catecholate complex having a formula of $H_gTi(L_1)(L_2)(L_3)$. $L_1$, $L_2$ and $L_3$ are ligands, and g is 1 or 2. At least one of $L_1$, $L_2$ and $L_3$ is a catecholate ligand or a substituted catecholate ligand.

In still other various embodiments, the present disclosure provides flow batteries incorporating an electrolyte solution containing a titanium catecholate complex that can lack a metal counterion.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
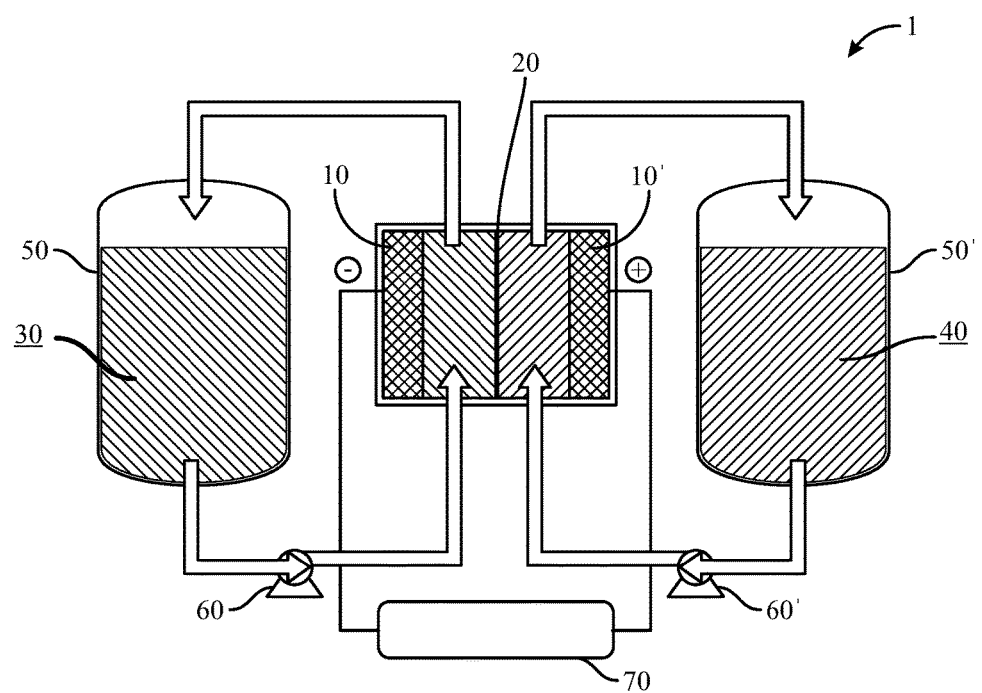
FIG. 1 depicts a schematic of an illustrative flow battery.

The present disclosure is directed, in part, to methods for forming titanium catecholate complexes in an aqueous solution. The present disclosure is also directed, in part, to compositions containing titanium catecholate complexes, including aqueous solutions of titanium catecholate complexes. The present disclosure is also directed, in part, to flow batteries containing an electrolyte solution containing a titanium catecholate complex.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure describes an electrochemical cell, flow battery, or other energy storage system, it is appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, conventional methods for producing titanium catecholate complexes can involve the use of expensive starting materials, which can be problematic for large-scale production operations and/or incompatible with aqueous reaction conditions. Titanium tetrachloride is a relatively low-cost titanium source, but the high reactivity of this material with water has conventionally precluded its use in aqueous methods for synthesizing titanium complexes. While titanium tetrachloride can be used in non-aqueous synthesis methods, the need for substantially anhydrous organic solvents in such methods can be problematic in terms of cost and scaleup. Although titanium catecholate complexes can be particularly desirable active materials for flow batteries, low-cost and scalable aqueous synthetic methods for these complexes are not believed to be presently known. In addition, presently available synthetic methods offer little opportunity for further purifying titanium catecholate complexes before their use. Hence, there remains considerable room for improving flow battery technology based upon titanium catecholate complexes. Exemplary description of illustrative flow batteries, their use, and operating characteristics is provided hereinbelow.

In contrast to conventional methods for synthesizing titanium coordination complexes, specifically titanium catecholate complexes, the present inventors discovered that titanium oxychloride ($TiOCl_2$) can be utilized as a convenient, relatively low-cost titanium source for forming such complexes in aqueous solutions, especially under acidic conditions. By virtue of their discovery that titanium oxychloride can be successfully utilized for forming titanium catecholate complexes, the inventors also discovered a route whereby even lower cost titanium tetrachloride can be used as an indirect precursor to synthesize such coordination complexes. While titanium tetrachloride reacts with water under typical reaction conditions to produce titanium dioxide and hydrogen chloride, under low-temperature conditions (e.g., between about −10° C. and about −40° C.) in the presence of limited amounts of water, titanium tetrachloride can form titanium oxychloride as a reaction product. The inventors discovered that this reaction product can be used with limited further modifications to form titanium catecholate complexes, as discussed herein. That is, the inventors further discovered that titanium tetrachloride can be used to generate titanium oxychloride in situ in the course of synthesizing titanium catecholate complexes in aqueous solutions. Hence, both titanium oxychloride and titanium tetrachloride allow low-cost and environmentally friendly aqueous synthetic processes for titanium catecholate complexes to be realized, thereby allowing the use of organic solvents to be eliminated or minimized.

Surprisingly, the inventors discovered that the synthesis of titanium catecholate complexes can take place under acidic conditions using titanium oxychloride as a titanium source. Ordinarily, titanium catecholate complexes are maintained in alkaline solution due to their higher stability at such pH values. Alkaline pH values can also deprotonate catecholate ligands to facilitate their coordination to titanium and other metals. Hence, the fact that coordination of catecholate ligands to titanium occurs under acidic conditions at all is surprising. Further, the acidic reaction conditions can, in at least some instances, promote precipitation of a protonated form of the titanium catecholate complexes that can be isolated and purified, if desired. By precipitating the titanium catecholate complexes, potential instability can be largely averted, and less hydrochloric acid can need to undergo neutralization in the course of readying an electrolyte solution for use. Conventional synthetic methods, in contrast, often provide solutions of titanium catecholate complexes in an alkali metal salt form, which are then generally used directly without undergoing further purification. The isolated and/or purified titanium catecholate complex can then be converted into a more soluble salt form for incorporation in a flow battery. The isolated and/or purified form of the titanium catecholate complexes can be lower in extraneous materials, such as acids or chloride ions, than are possible by other synthetic methods, at least without conducting laborious purification operations on the initial titanium catecholate complex. Therefore, the methods of the present disclosure offer the further opportunity to improve flow battery performance through ready access to high purity electrolyte solutions containing titanium catecholate complexes. High purity electrolyte solutions can be desirable for improving durability and operating performance of flow batteries and related electrochemical systems. If extraneous salts or other materials can be tolerated in the intended end use of the titanium catecholate complex, however, the protonated form of the titanium catecholate complex can be used directly.

Although catecholate ligands can produce titanium complexes with desirable electrochemical properties, these ligands are relatively hydrophobic and can lead to electrolyte solutions having relatively low concentrations of active material. Substituted catecholate ligands bearing one or more solubilizing groups can lead to electrolyte solutions having higher concentrations of active material. Advantageously, the methods of the present disclosure utilizing titanium oxychloride or titanium tetrachloride are fully compatible with both unsubstituted catecholate ligands and various types of substituted catecholate ligands. Accordingly, the methods of the present disclosure can provide still further improvement in flow battery performance by allowing higher concentration electrolyte solutions to be prepared. Further discussion of suitable substituted catecholate ligands is provided hereinbelow. Advantageously, such substituted catecholate ligands can be produced synthetically by relatively simple series of organic reactions.

Accordingly, the present disclosure provides various methods directed to the preparation of titanium catecholate complexes using titanium oxychloride or titanium tetrachloride as a titanium source. Compositions containing such titanium catecholate complexes, electrolyte solutions containing such titanium catecholate complexes, and flow batteries containing such titanium catecholate complexes are also disclosed herein.

In various embodiments, methods of the present disclosure can include combining one or more catecholate ligands and titanium oxychloride in an aqueous solution, and reacting the one or more catecholate ligands with the titanium oxychloride in the aqueous solution to form a titanium catecholate complex.

The term "titanium oxychloride" may be referred to synonymously as a "solution comprising titanium (IV) chloride hydrochloride." Such solutions are described by CAS number 92334-13-3 and are available from several suppliers, such as Cristal. Typically, such solutions exhibit a pH of about 1 or less. Accordingly, in some embodiments, a solution of titanium oxychloride can be used in preparing the aqueous solution from which the titanium catecholate complex is subsequently formed. Formation of the titanium catecholate complex can then take subsequently by employing the further conditions set forth below.

In some or other embodiments, the titanium oxychloride can be formed in situ in the course of providing the aqueous solution. More specifically, the titanium oxychloride can be formed in situ from titanium tetrachloride. Accordingly, in some embodiments, methods of the present disclosure can include combining titanium tetrachloride with water at conditions under which the titanium tetrachloride reacts with the water to form the titanium oxychloride. Suitable conditions for forming titanium oxychloride from titanium tetrachloride are set forth in more detail hereinafter. In some embodiments, the conditions for forming titanium oxychloride can be such that titanium dioxide is not formed in the aqueous solution. Optionally, in some or other embodiments, methods of the present disclosure can include diluting the titanium oxychloride to form the aqueous solution. Dilution, for example, can be used to reach a desired pH in the aqueous solution for forming the titanium catecholate complex. Aqueous acids and/or bases can also be used to adjust the pH value, as discussed hereinafter.

In general, the reaction between titanium tetrachloride and water proceeds to titanium oxychloride in the presence of limited quantities of water and/or at low reaction temperatures. Hydrogen chloride is also formed as a co-product in this process. Suitable conditions for forming an aqueous solution of titanium oxychloride from titanium tetrachloride are described in more detail in U.S. Pat. No. 3,425,796, which is incorporated herein by reference in its entirety. More particular conditions for producing titanium oxychloride can include cooling titanium tetrachloride to about −25° C. to about −30° C., or even to about −40° C., and adding ice at a rate such that there is substantially no liquid water present and the temperature of the reaction mixture does not rise above the melting point of the ice. Chipped, shaved or flaked ice can be particularly suitable for controlling the reaction rate and maximizing the amount of solid reactant surface area. As the ice is added, a frothy, semi-solid phase can form. Agitation can be conducted to facilitate removal of the gaseous hydrogen chloride co-product. Even with removal of gaseous hydrogen chloride, a solution of titanium oxychloride produced upon dilution with water can have a pH of less than about 1. In some embodiments, the pH of the titanium oxychloride solution can be adjusted with an aqueous base before adding the one or more catecholate ligands to promote complex formation. For example, in some embodiments, the pH can be raised to a range between about 2.5 and about 7, or between about 3 and about 4.

In some embodiments of the present disclosure, the titanium tetrachloride can be reacted with the water at a temperature below about 0° C. In more specific embodiments, the titanium tetrachloride can be reacted with the water at a temperature ranging between about −10° C. and about −40° C., or at a temperature ranging between about −20° C. and about −30° C., or at a temperature ranging between about −25° C. and about −30° C. Temperatures within the foregoing ranges can be maintained with refrigeration, ice-salt mixtures, or cryogenic baths as deemed appropriate by one having ordinary skill in the art.

In more specific embodiments, methods of the present disclosure can include cooling titanium tetrachloride to a temperature below about 0° C., particularly in a range between about −10° C. and about −40° C. and adding water to the cooled titanium tetrachloride. More particularly, water in the form of ice can be added to the cooled titanium tetrachloride. The titanium tetrachloride can likewise be in a solid form at these temperatures.

Once the titanium tetrachloride and water have been combined and reacted to form the titanium oxychloride, the titanium oxychloride can be further diluted with water to form the aqueous solution in some embodiments of the present disclosure. The titanium oxychloride concentration in the aqueous solution can be dictated, at least in part, by whether one wants to maintain the titanium catecholate complex in solution or precipitate it. For example, higher titanium oxychloride solutions can be more favorable for promoting precipitation. Suitable concentrations of titanium oxychloride in the aqueous solution can range between about 0.1 M and about 3 M, or between about 0.5 M and about 2.5 M, or between about 1 M and about 2 M.

As discussed above, the as-produced pH values of titanium oxychloride solutions can often be about 1 or less. Accordingly, in some embodiments, methods of the present disclosure can include raising the pH of the aqueous solution containing the titanium oxychloride before forming the titanium catecholate complex. Such pH adjustment can take place with a base before the at least one catecholate ligand is added to the aqueous solution. The added base can be in a solid or liquid form. In some embodiments, the pH of the aqueous solution can range between about 2.5 and about 7. In more particular embodiments, the pH of the aqueous solution can range between about 3 and about 6, or between about 3 and about 5, or between about 3 and about 4, or between about 4 and about 5. Such modestly acidic pH values can promote precipitation of a protonated or "salt-free" form of the titanium catecholate complex in some cases, as discussed hereinafter.

In various embodiments, the titanium oxychloride can be combined with the aqueous solution or generated in situ within the aqueous solution before the one or more catecholate ligands are added thereto. Accordingly, in more specific embodiments, methods of the present disclosure can include combining the one or more catecholate ligands with the aqueous solution after the titanium oxychloride has been formed. By having the titanium oxychloride present in the aqueous solution and ready to undergo complexation before the at least one catecholate ligand is added, the time during which potentially unstable free ligands are present can be minimized.

In some embodiments, combining the one or more catecholate ligands with the aqueous solution can include adding the one or more catecholate ligands to the aqueous solution. The one or more catecholate ligands can be added to the aqueous solution in solid form or dissolved in a solution (e.g., a solution in water or a mixture of water and a water-miscible organic solvent). In other embodiments, combining the one or more catecholate ligands with the aqueous solution can include adding the aqueous solution to the one or more catecholate ligands. Again, the one or more catecholate ligands can be in a solid form or dissolved in solution in such embodiments. In the foregoing embodiments, aqueous slurries of the one or more catecholate ligands are considered to constitute a solid form.

In more specific embodiments, the titanium catecholate complex produced by the methods of the present disclosure can have a formula of

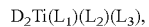

$$D_2Ti(L_1)(L_2)(L_3),$$

wherein D is H, $NH_4^+$, $NR_4^+$ (R=alkyl), $Li^+$, $Na^+$, $K^+$, or any combination thereof; and $L_1$, $L_2$ and $L_3$ are ligands, at least one of $L_1$, $L_2$ or $L_3$ being a catecholate ligand or a substituted catecholate ligand. These terms will refer herein to both the unbound and metal-bound forms of these substances. Titanium catecholate complexes having this type of formula can be obtained when each of $L_1$, $L_2$ and $L_3$ are chelating ligands. As discussed herein, the protonated form (i.e., D=H) of the titanium catecholate complexes can sometimes be obtained directly from the aqueous solution under mildly acidic conditions. In further embodiments, a salt form of the titanium catecholate complexes can be obtained by reacting the initially produced protonated form with one or more aqueous bases. Aqueous bases containing monovalent cations (e.g., $NH_4^+$, $Li^+$, $Na^+$, or $K^+$) can be particularly advantageous for incorporation in the electrolyte solution of a flow battery. Other aqueous bases, including those containing divalent cations, can be suitable for various alternative applications. If the protonated form of the titanium catecholate complex precipitates, it can be added to the aqueous base and undergo reaction and dissolution to form an alternative salt form. If no precipitation occurs, the aqueous base can be added to the aqueous solution in which the reaction occurred until a desired pH has been reached and a different salt form has been produced in situ.

In alternative embodiments, D can be a divalent metal ion, a trivalent metal cation, or a tetraalkylammonium cation. Although monovalent metal cations such as alkali metal cations (e.g., $Li^+$, $Na^+$, $K^+$, or any combination thereof) can be desirable for inclusion in the electrolyte solution of a flow battery, other counterion forms can be desirable for other purposes. For example, alternative counterion forms can be desirable for purification purposes in some instances. Conversion to a monovalent counterion form can take place following isolation and purification, if needed.

In some embodiments, one of $L_1$, $L_2$ and $L_3$ can be a catecholate ligand or a substituted catecholate ligand. In some embodiments, two of $L_1$, $L_2$ and $L_3$ can be a catecholate ligand or a substituted catecholate ligand. In still other embodiments, each of $L_1$, $L_2$ and $L_3$ can be a catecholate ligand or a substituted catecholate ligand. Any combination of catecholate ligands and substituted catecholate ligands can be used in the foregoing embodiments. For example, the titanium catecholate complexes can contain one substituted catecholate ligand and two unsubstituted catecholate ligands in some embodiments of the present disclosure. Other suitable ligands that can present in conjunction with catecholate ligands and/or substituted catecholate ligands are presented hereinbelow.

As used herein, the term "substituted catecholate" will refer to a catechol compound (i.e., 1,2-dihydroxybenzene) in which at least one aromatic ring position has been substituted with an additional functional group, such as heteroatom functional group. As used herein, the term "heteroatom functional group" will refer to any grouping of atoms that contains O, N or S. Heteroatom functional group(s) can improve solubility of catecholate ligands and their resulting titanium coordination complexes. Some suitable examples of heteroatom-substituted catecholates are discussed in detail hereinafter.

In some embodiments, suitable substituted catecholate ligands can include, for example, catechol compounds containing one or more alkyl, alkenyl, alkynyl, carboxylic acid, carboxylic ester, amide, formyl, cyano, halo, hydroxyl, sulfonate, sulfonic acid, phosphonate, or phosphonic acid functional groups. In some embodiments, suitable substituted catecholate ligands can contain one functional group. In some embodiments, substituted catecholate ligands containing a single functional group can have the functional group present in the 4-position of the aromatic ring. However, substituted catecholate ligands can bear functionality in any open ring position. In some or other embodiments, suitable substituted catecholate ligands can contain two additional functional groups. In more particular embodiments, suitable substituted catecholate ligands can contain one or two sulfonic acid groups. Catecholate ligands containing sulfonic acid groups can be particularly desirable for increasing the solubility of the titanium catecholate complexes. Hydroxycatechols and carboxycatechols can be of similar interest in this regard.

In some or other more particular embodiments, substituted catecholate ligands suitable for use in the methods of the present disclosure can include those having a structure of

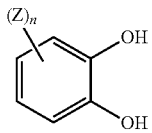

in a neutral form or a salt form. Z is a heteroatom functional group selected from the group consisting of $A^1R^{41}$, $A^2R^{42}$, $A^3R^{43}$, CHO, and sulfonic acid. Variable n is an integer ranging between 1 and 4, such that one or more Z are bound to the substituted catecholate ligand at an open aromatic ring position. Each Z is the same or different when more than one Z is present. $A^1$ is $—(CH_2)_a—$ or $—(CHOR)(CH_2)_a—$, $R^{41}$ is $—OR^1$ or $—(OCH_2CH_2O)_bR^1$, a is an integer ranging between 0 and about 6, with the proviso that $R^1$ is not H when a is 0 and $R^{41}$ is $—OR^1$, and b is an integer ranging between 1 and about 10. $A^2$ is $—(CH_2)_c—$ or $—CH(OR^2)(CH_2)_d$, $R^{42}$ is $—NR^3R^4$, a carbon-linked amino acid, or $—C(=O)XR^5$, X is $—O—$ or $—NR^6—$, c is an integer ranging between 0 and about 6, and d is an integer ranging between 0 and about 4. $A^3$ is $—O—$ or $—NR^2—$, $R^{43}$ is $—(CHR^7)_eOR^1$, $—(CHR^7)_eNR^3R^4$, $—(CHR^7)_eC(=O)XR^5$, or $—C(=O)(CHR^7)_fR^8$, e is an integer ranging between 1 and about 6, with the proviso that e is not 1 when $A^3$ is $—O—$, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or $—(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or $—(OCH_2CH_2O)_bR^1$.

With regard to the term "salt form," it is to be understood that this term is directed to any functionalities in Z that may be protonated or deprotonated. Similarly, the term "neutral form" is to be understood in regard to Z being uncharged. For any particular chemical structures of substituted catecholate ligands shown herein, the protonated "free ligand" form will be shown as a matter of convenience.

The substituted catecholate ligands of the present disclosure can have one, two, three or four Z heteroatom functional groups substituting the open positions of the aromatic ring. When more than one Z is present, each Z heteroatom functional group can be the same or different. In more specific embodiments, the substituted catecholate ligand can have one, two or three Z heteroatom functional groups, such that its structure is among those shown below.

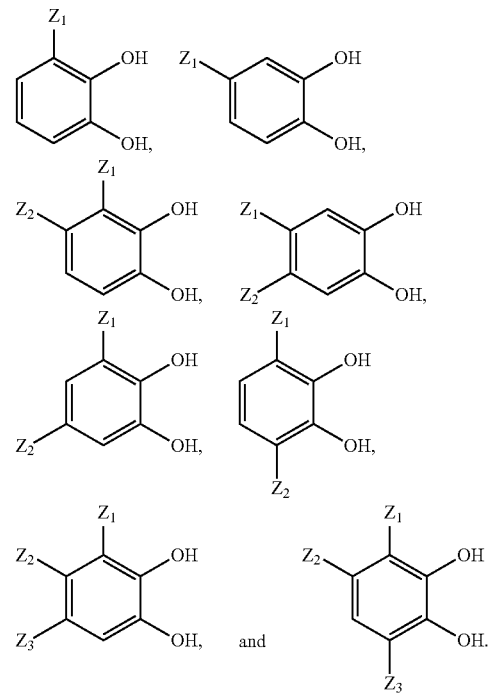

In still more specific embodiments, the substituted catecholate ligand can have one Z functionality, such that its structure is among

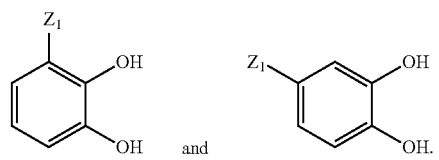

In yet still more specific embodiments, the substituted catecholate ligand can have a formula of

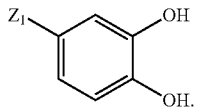

As indicated above, Z can include various heteroatom functional groups that can improve the solubility of the substituted catecholate ligands and their coordination compounds. Illustrative examples of various classes of substituted catecholate ligands incorporating such heteroatom functional groups follows hereinafter.

In some embodiments, Z can be $A^1R^{41}$, wherein $A^1$ is —$(CH_2)_a$— or —$(CHOR)(CH_2)_a$—, $R^{41}$ is —$OR^1$ or —$(OCH_2CH_2O)_bR^1$, a is an integer ranging between 0 and about 6, and b is an integer ranging between 1 and about 10. When $A^1$ is —$(CH_2)_a$— and a is 0, it is to be understood that $R^{41}$ is bound directly to the aromatic ring of the substituted catecholate. Similarly, when $A^1$ is —$(CHOR)(CH_2)_a$— and a is 0, it is to be understood that $R^{41}$ is bound indirectly to the aromatic ring by an intervening —(CHOR) group. In some embodiments of the present disclosure, a can be 0. In other various embodiments of the present disclosure, a can range between 1 and 6, or between 1 and 4, or between 0 and 4, or between 1 and 3.

In the substituted catecholate ligands of the present disclosure, R is H, $C_1$-$C_6$ alkyl, heteroatom-substituted $C_1$-$C_6$ alkyl, or $C_1$-$C_6$ carboxyalkyl, and $R^1$ is H, methyl, ethyl, a $C_3$-$C_6$ alkyl, a heteroatom-substituted $C_3$-$C_6$ alkyl, a $C_2$-$C_6$ polyol bound through an ether linkage or an ester linkage, or $C_1$-$C_6$ carboxyalkyl. That is, at least a portion of $R^{41}$ can be defined by a polyol structure that is bound through an ether linkage or an ester linkage to the remainder of the structure of $R^{41}$, to $A^1$, or to the aromatic ring of the substituted catecholate ligand. Exemplary polyols and their various modes of binding are discussed further below. Illustrative $C_1$-$C_6$ alkyl groups that can be present in any of the various embodiments of the present disclosure can include, for example, methyl, ethyl, propyl, isopropyl, butyl, sec-butyl, tert-butyl, pentyl, isopentyl, neopentyl, 2,2-dimethylbutyl, hexyl, isohexyl, and the like. As used herein, the term "heteroatom-substituted $C_1$-$C_6$ alkyl" will refer to a straight-chain or branched-chain alkyl group that has had one or more of its hydrogen atoms replaced by an oxygen- or nitrogen-containing functional group. "Heteroatom-substituted $C_1$-$C_6$" will also refer to a straight-chain or branched-chain alkyl group that has had one of its backbone carbon atoms and its accompanying hydrogen atoms replaced by an oxygen- or nitrogen-containing functional group.

In some embodiments, with regard to $A^1R^{41}$, the following proviso is to be made: $R^1$ is not H when a is 0 and $R^{41}$ is —OR'.

As used herein, the term "polyol" will refer to any compound having two or more alcohol functional groups. Additional heteroatom functionality, such as amines and carboxylic acids, can optionally be present within a polyol. Thus, amino alcohol and hydroxy acid analogues of unmodified glycols and higher polyols are also encompassed by the term "polyol." As used herein, the term "higher polyol" will refer to a polyol having more than two alcohol functional groups. Illustrative polyols that can be present within $R^{41}$ include any $C_2$-$C_6$ polyol, including glycols, higher polyols, and monosaccharides. As with the term "polyol," the term "monosaccharide" is to be understood to also include both the base monosaccharide and the corresponding sugar alcohols, sugar acids, and deoxy sugars of the base monosaccharide, including any open- or closed-chain forms of these materials.

Illustrative polyols that can be present in the various embodiments of the present disclosure include, for example, 1,2-ethanediol (ethylene glycol), 1,2-propanediol (propylene glycol), 1,3-propanediol, 1,2-butanediol, 1,4-butanediol, glycerol, erythritol, threitol, arabitol, xylitol, ribitol, mannitol, sorbitol, galacitol, fucitol, iditol, inositol, glycolaldehyde, glyceraldehyde, 1,3-dihydroxyacetone, erythrose, threose, erythrulose, arabinose, ribose, lyxose, xylose, ribulose, xylulose, allose, altrose, glucose, mannose, gulose, idose, galactose, talose, psicose, fructose, sorbose, tagatose, deoxyribose, rhamnose, fucose, glyceric acid, xylonic acid, gluconic acid, ascorbic acid, glucuronic acid, galacturonic acid, iduronic acid, tartaric acid, galactaric acid, and glucaric acid. Any enantiomeric and/or diastereomeric forms of these compounds are also encompassed within the term "polyol" in the present disclosure, as well as their open- or closed-ring forms, if formed.

More particular embodiments in regard to $A^1R^{41}$ can include, for example, those in which a is 0 or 1, $A^1$ is —$(CH_2)$—$_a$ and $R^{41}$ is —$OR^1$ with the above proviso being made in some embodiments; and a is 0 or 1, $A^1$ is —$(CH_2)_a$— and $R^{41}$ is —$(OCH_2CH_2O)_bR^1$.

In still more particular embodiments in regard to $A^1R^{41}$, suitable substituted catecholate ligands can include the following:

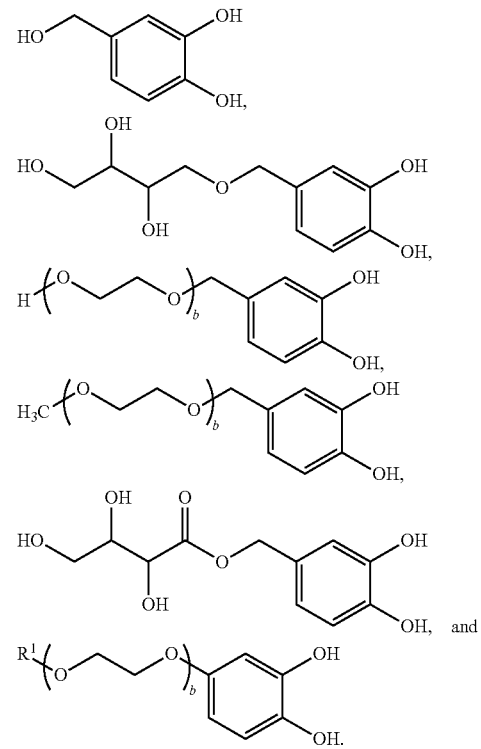

In some embodiments, Z can be $A^2R^{42}$, wherein $A^2$ is —$(CH_2)_c$— or —$(CH_2OR^2)(CH_2)_d$—, $R^{42}$ is —$NR^3R^4$, a carbon-linked amino acid, or —$C(=O)XR^5$, X is —O— or —$NR^6$—, c is an integer ranging between 0 and about 6, d is an integer ranging between 0 and about 4. $R^2$, $R^3$, $R^4$ and $R^6$ are independently selected from the group consisting of H, $C_1$-$C_6$ alkyl, or heteroatom-substituted $C_1$-$C_6$ alkyl. Likewise, $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —(CH$_2$CH$_2$O)$_b$R$^1$, wherein $R^1$ is defined as above. In some embodiments, c can range between 0 and 4, or between 1 and 5, or between 1 and 4, or between 1 and 3. In some embodiments, d can range between 0 and 3, or between 0 and 2, or between 1 and 3.

With regard to carbon-linked amino acids, the amino acids can be carbon-linked by their alpha carbon in various embodiments (i.e., adjacent to the carboxylate and amino functionalities). As used herein, the term "amino acid" will refer to any group of atoms containing at least one amine group and one carboxylic acid group, optionally in protected form. In more specific embodiments, the term "amino acid" will refer to naturally occurring amino acids in their D- or L-forms, including oligomers thereof. Illustrative naturally occurring amino acids that can be present include, for example, arginine, histidine, lysine, aspartic acid, glutamic acid, serine, threonine, asparagine, glutamine, cysteine, glycine, proline, alanine, valine, isolucine, leucine, methionine, phenylalanine, tyrosine, and tryptophan, as well as synthetic derivatives thereof. These amino acids and others can be present in ester-linked or amide-linked forms as discussed further hereinbelow.

More particular embodiments in regard to $A^2R^{A2}$ can include, for example, those in which $A^2$ is —(CH$_2$)$_c$—, c is an integer ranging between 1 and 6, or between 1 and 3, and $R^{A2}$ is —NR$^3$R$^4$ in which $R^3$ and $R^4$ are H or CH$_3$; $A^2$ is —(CH$_2$)$_c$—, c is 0, and $R^{A2}$ is —NR$^3$R$^4$ in which $R^3$ and $R^4$ are H or CH$_3$; $A^2$ is —(CH$_2$)$_c$—, c is 0, and $R^{A2}$ is —C(=O)XR$^5$ in which X is O and $R^5$ is a $C_2$-$C_6$ polyol bound through an ester linkage, a hydroxyacid bound through an ester linkage, a polyglycol acid bound through an ester linkage, an amino alcohol bound through an ester linkage, or an amino acid bound through an ester linkage; $A^2$ is —CH(OR$^2$)(CH$_2$)$_d$—, $R^2$ is H, d is an integer ranging between 1 and 4, and $R^{A2}$ is —NR$^3$R$^4$ in which $R^3$ and $R^4$ are H or CH$_3$; and $A^2$ is —CH(OR$^2$)(CH$_2$)$_d$—, $R^2$ is H, d is an integer ranging between 1 and 4, and $R^{A2}$ is —C(=O)XR$^5$ in which X is O and $R^5$ is a $C_2$-$C_6$ polyol bound through an ester linkage, a hydroxyacid bound through an ester linkage, a polyglycol acid bound through an ester linkage, an amino alcohol bound through an ester linkage, or an amino acid bound through an ester linkage.

In still more particular embodiments in regard to $A^2R^{A2}$, suitable substituted catecholate ligands can include the following:

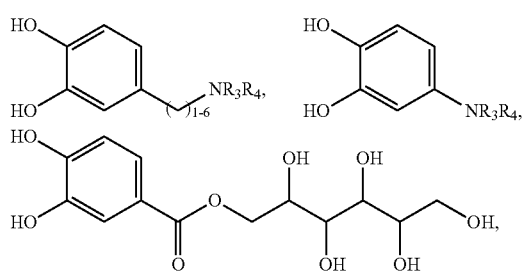

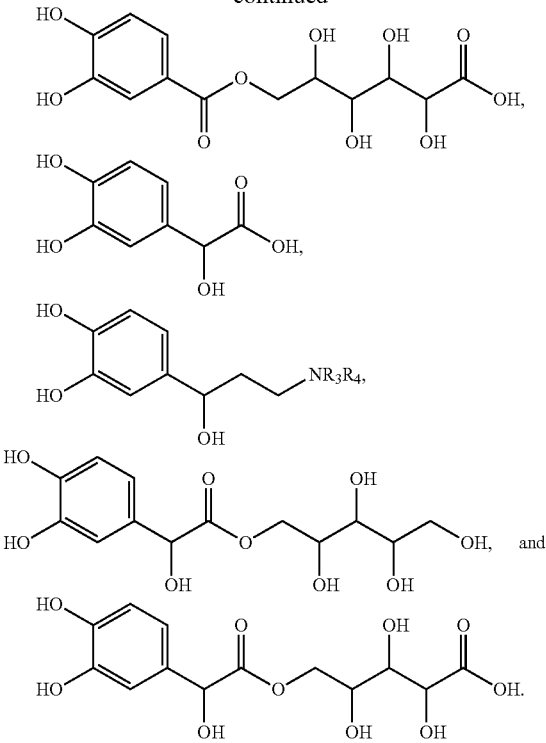

In some embodiments, Z can be $A^3R^{A3}$, wherein $A^3$ is —O— or —NR$^2$—, $R^{A3}$ is —(CHR$^7$)$_e$OR$^1$, —(CHR$^7$)$_e$NR$^3$R$^4$, —(CHR$^7$)$_e$C(=O)XR$^5$, or —(C=O)(CHR$^7$)$_f$R$^8$, e is an integer ranging between 1 and about 6, f is an integer ranging between 0 and about 6, $R^7$ is H or OH, and $R^8$ is h, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —(OCH$_2$CH$_2$O)$_b$R$^1$. In other various embodiments of the present disclosure, e can range between 2 and 6, or between 1 and 4, or between 1 and 3. In other various embodiments of the present disclosure, f can range between 1 and 6, or between 1 and 4, or between 0 and 4, or between 1 and 3.

With regard to $A^3R^{A3}$, the following proviso is to be made: e is not 1 when $A^3$ is —O—.

More particular embodiments in regard to $A^3R^{A3}$ can include, for example, those in which $A^3$ is —O—, $R^{A3}$ is —(CHR$^7$)$_e$OR$^1$, and e is an integer ranging from 2 to 6; $A^3$ is —O—, $R^{A3}$ is —(CHR$^7$)$_e$NR$^3$R$^4$, and e is an integer ranging from 1 to 6; $A^3$ is —O—, $R^{A3}$ is —(CHR$^7$)$_e$C(=O)OR$^5$, and e is an integer ranging from 2 to 6; and $A^3$ is —O—, $R^{A3}$ is —C(=O)(CHR$^7$)$_f$R$^8$, and f is an integer ranging from 0 to 6 or from 1 to 6.

In still more particular embodiments in regard to $A^3R^{A3}$, suitable substituted catecholate ligands can include the following:

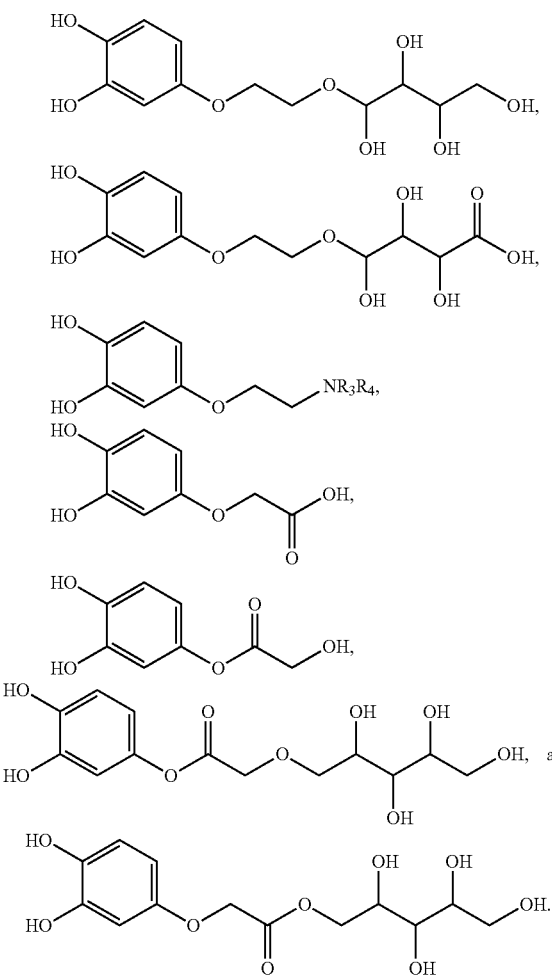

In still other various embodiments of the present disclosure, the substituted catecholate ligand of the present disclosure can have one or more Z that is CHO, as shown in the exemplary structure below.

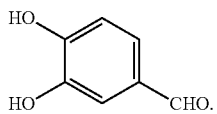

In other more specific embodiments of the present disclosure, the substituted catecholate ligand can have a structure selected from among the following:

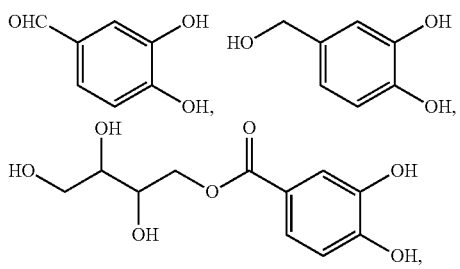

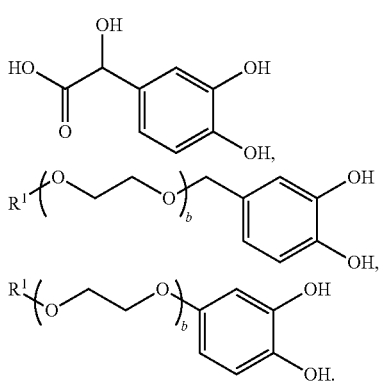

In other more specific embodiments of the present disclosure, the substituted catecholate ligand can have a structure selected from among the following

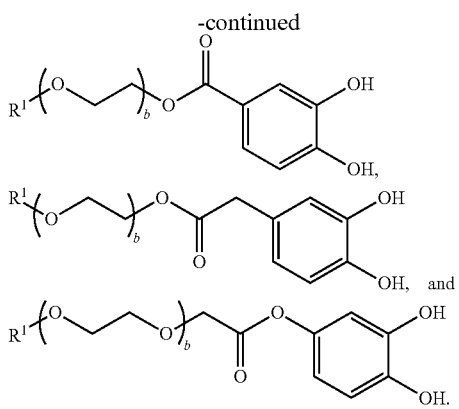

In still other various embodiments of the present disclosure, the substituted catecholate ligand can be 3,4-dihydroxymandelic acid, which has a structure of

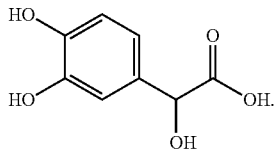 [SMILES: O=C(O)C(O)c1ccc(O)c(O)c1]

In more specific embodiments, the titanium catecholate complex can have a formula of $D_2Ti(L_1)(L_2)(L_3)$, wherein D is H, $NH_4^+$, $NR_4^+$, $Li^+$, $Na^+$, $K^+$, or any combination thereof; and $L_1$, $L_2$ and $L_3$ are ligands, with at least one of $L_1$, $L_2$ or $L_3$ being a substituted catecholate ligand. Suitable substituted catecholate ligands include those described above. In some embodiments, each of $L_1$, $L_2$ and $L_3$ can be a catecholate ligand or a substituted catecholate ligand.

In some or other more specific embodiments, the titanium catecholate complex can have a formula of $H_2Ti(L_1)(L_2)(L_3)$, wherein $L_1$, $L_2$ and $L_3$ are ligands, and at least one of $L_1$, $L_2$ $L_3$ is a catecholate ligand or a substituted catecholate ligand. Suitable substituted catecholate ligands can include those described above. In some embodiments, each of $L_1$, $L_2$ and $L_3$ can be a catecholate ligand or a substituted catecholate ligand. As indicated above, such titanium catecholate complexes can be suitably isolated from the aqueous solution as a solid in some embodiments. Specifically, such titanium catecholate complexes can precipitate from the aqueous solution as they are formed in many instances. Subsequently, the precipitated titanium catecholate complexes can be isolated in solid form, such as by decantation, filtration, centrifugation, or the like.

Upon obtaining a titanium catecholate complex in solid form with a formula of $H_2Ti(L_1)(L_2)(L_3)$, as defined above, the complex can be further purified in some embodiments. In some embodiments, the solid form of the complex can be washed with water or a suitable washing solvent in which the titanium catecholate complex is substantially insoluble. In some or other embodiments, the titanium catecholate complex can be recrystallized in order to affect its further purification. In alternative embodiments, the solid form of the titanium catecholate complex can be used "as-formed" without undergoing further purification.

In some embodiments, a titanium catecholate complex in solid form with a formula of $H_2Ti(L_1)(L_2)(L_3)$, as defined above, can be further converted into another salt form in some embodiments. Specifically, in some embodiments, methods of the present disclosure can further include reacting the titanium catecholate complex with an aqueous base to form a salt of the titanium catecholate complex. Suitable aqueous bases can include, for example, ammonium hydroxide, lithium hydroxide, sodium hydroxide, potassium hydroxide, the like, and any combination thereof. The corresponding carbonate and bicarbonate salts can be used similarly. Accordingly, in such embodiments, the titanium catecholate complex can be obtained in a salt form having a formula of $D_2Ti(L_1)(L_2)(L_3)$, wherein D is $NH_4^+$, $NR_4^+$, $Li^+$, $Na^+$, $K^+$, or any combination thereof; and $L_1$, $L_2$ and $L_3$ are ligands as defined as above. In some embodiments D can be a mixture of $Na^+$ and $K^+$ cations, such as an approximately 1:1 mixture of these cations. Cation mixtures, such as a mixture of $Na^+$ and $K^+$, can be particularly desirable for purposes of increasing solubility of the titanium catecholate complexes. In addition to the monovalent cations set forth previously, aqueous bases containing divalent cations can be utilized in a related manner, particularly in instances where the complex is not intended for use in an electrolyte solution of a flow battery.

In various embodiments, the titanium catecholate complex can be dissolved in aqueous solution that has an alkaline pH after adding the aqueous base. In some embodiments, the alkaline pH can reside in a range of about 9 to about 12, which can be particularly desirably for promoting stability and solubility of the titanium catecholate complex. These pH conditions can also be particularly compatible for use in conjunction with flow batteries and their various components. Other suitable alkaline pH ranges can include, for example, about 7 to about 7.5, or about 7.5 to about 8, or about 8 to about 8.5, or about 8.5 to about 9, or about 9.5 to about 10, or about 10 to about 10.5, or about 10.5 to about 11, or about 11 to about 11.5, or about 11.5 to about 12, or about 12 to about 12.5, or about 12.5 to about 13, or about 13 to about 13.5, or about 13.5 to about 14.

In still other various embodiments, titanium catecholate complexes having a formula of $D_2Ti(L_1)(L_2)(L_3)$ wherein D is H, $NH_4^+$, $NR_4^+$, $Li^+$, $Na^+$, $K^+$, or any combination thereof can be undergo reduction to produce titanium catecholate complexes having a formula of $DTi(L_1)(L_2)(L_3)$ wherein D is H, $NH_4^+$, $NR_4^+$, $Li^+$, $Na^+$, $K^+$, or any combination thereof; and $L_1$, $L_2$ and $L_3$ are defined as above. That is, both the oxidized (i.e., $Ti^{4+}$) and reduced (i.e., $Ti^{3+}$) forms of the titanium catecholate complexes can be produced according to the various embodiments of the present disclosure.

Accordingly, in more specific embodiments of the present disclosure, methods for forming a titanium catecholate complex can include: combining titanium oxychloride and at least about 3 equivalents of at least one catecholate ligand or substituted catecholate ligand in water to form an aqueous solution, and reacting the at least one catecholate ligand or substituted catecholate ligand with the titanium oxychloride to produce a compound having a formula of $H_2Ti(L_1)(L_2)(L_3)$ wherein $L_1$, $L_2$ and $L_3$ are a catecholate ligand or a substituted catecholate ligand. In some embodiments, the methods can further include isolating the titanium catecholate complex having the formula of $H_2Ti(L_1)(L_2)(L_3)$ as a solid. In some or other further embodiments, the methods can further include reacting the titanium catecholate complex having the formula of $H_2Ti(L_1)(L_2)(L_3)$ with an aqueous base to form a titanium catecholate complex having a formula of $$D_2Ti(L_1)(L_2)(L_3)$$

wherein D is $NH_4^+$, $NR_4+$, $Li^+$, $Na^+$, $K^+$, or any combination thereof, and $L_1$, $L_2$ and $L_3$ are a catecholate ligand or a substituted catecholate ligand.

Similarly, in other more specific embodiments of the present disclosure, methods for forming a titanium catecholate complex can include: combining titanium tetrachloride and water at conditions under which the titanium tetrachloride reacts with the water to form titanium oxychloride, forming an aqueous solution with the titanium oxychloride, adding at least about 3 equivalents of at least one catecholate ligand or substituted catecholate ligand to the aqueous solution, and reacting the at least one catecholate ligand or substituted catecholate ligand with the titanium oxychloride to produce a compound having a formula of $$H_2Ti(L_1)(L_2)(L_3)$$

wherein $L_1$, $L_2$ and $L_3$ are a catecholate ligand or a substituted catecholate ligand. In some embodiments, the methods can further include isolating the titanium catecholate complex having the formula of $H_2Ti(L_1)(L_2)(L_3)$ as a solid. In some or other further embodiments, the methods can further include reacting the titanium catecholate complex having the formula of $H_2Ti(L_1)(L_2)(L_3)$ with an aqueous base to form a titanium catecholate complex having a formula of $$D_2Ti(L_1)(L_2)(L_3)$$

wherein D is $NH_4^+$, $NR_4^+$, $Li^+$, $Na^+$, $K^+$, or any combination thereof, and $L_1$, $L_2$ and $L_3$ are a catecholate ligand or a substituted catecholate ligand.

In some embodiments, titanium catecholate complexes of the present disclosure can include other ligands in combination with the at least one catecholate ligand or substituted catecholate ligand. Any ligands that are not a catecholate ligand or substituted catecholate ligand can include, for example, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that the additional ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of monodentate ligands that can optionally be present in the titanium catecholate complexes include, for example, halides, cyanide, carbonyl or carbon monoxide, nitride, oxo, hydroxo, water, sulfide, thiols, pyridine, pyrazine, and the like. Other examples of bidentate ligands that can optionally be present in the titanium catecholate complexes of the present disclosure include, for example, bipyridine, bipyrazine, ethylenediamine, diols (including ethylene glycol), and the like. Other examples of tridentate ligands that can optionally be present in the titanium catecholate compounds of the present disclosure include, for example, terpyridine, diethylenetriamine, triazacyclononane, tris(hydroxymethyl)aminomethane and the like. Other acceptable ligands can include quinones, hydroquinones, viologens, acridinium, polycyclic aromatic hydrocarbons and combinations thereof.

As discussed above, the methods of the present disclosure can provide titanium catecholate complexes that differ in composition and/or purity compared to those made through alternative synthetic methods. Accordingly, in various embodiments, the present disclosure provides compositions containing a titanium catecholate complex as described herein. In more specific embodiments, compositions of the present disclosure can include titanium catecholate complexes having a formula of $$H_gTi(L_1)(L_2)(L_3),$$

wherein g is 1 or 2, and $L_1$, $L_2$ and $L_3$ are ligands, at least one of $L_1$, $L_2$ and $L_3$ being a catecholate ligand or a substituted catecholate ligand. The oxidized form of the titanium catecholate complex (i.e., g=2) can be produced directly from the aqueous solution, and the reduced form of the titanium catecholate complex (i.e., g=1) can be formed following reduction. More particular configurations for titanium catecholate complexes are provided hereinabove.

In some or other various embodiments, electrolyte solutions of the titanium catecholate complexes are also described herein. That is, in some embodiments, compositions of the present disclosure can further include an aqueous solution in which the titanium catecholate complex is disposed. In some embodiments, the aqueous solution can be an alkaline solution. In some or other embodiments, the aqueous solution can be a substantially neutral solution in water.

In still other various embodiments, flow batteries are described herein. The flow batteries can incorporate an electrolyte solution including at least one titanium catecholate complex, as defined hereinabove. That is, flow batteries of the present disclosure can include an electrolyte solution containing the various compositions described hereinabove as an active material. Exemplary disclosure is presented hereinbelow regarding illustrative flow batteries and their operating characteristics when employing the presently disclosed electrolyte solutions.

In more specific embodiments, the electrolyte solutions of the present disclosure can be an aqueous electrolyte solution. An aqueous electrolyte solution will refer herein to any solution in which water is the predominant component, including solutions containing a water-miscible organic solvent as a minority component. Illustrative water-miscible organic solvents that can be present include, for example, alcohols and glycols, optionally in the presence of one or more surfactants. In more specific embodiments, an aqueous electrolyte solution can contain at least about 98% water by weight. In other more specific embodiments, an aqueous electrolyte solution can contain at least about 55% water by weight, or at least about 60% water by weight, at least about 65% water by weight, at least about 70% water by weight, at least about 75% water by weight, at least about 80% water by weight, at least about 85% water by weight, at least about 90% water by weight, or at least about 95% water by weight.

In some embodiments, the aqueous electrolyte solution can be free of water-miscible organic solvents and consist of water alone as a solvent.

In addition to a solvent and the active materials described above, the aqueous electrolyte solutions of the present disclosure can include one or more mobile ions. In some embodiments, mobile ions can include proton, hydronium, or hydroxide. In other various embodiments of the present disclosure, one can transport ions other than proton, hydronium, or hydroxide, either alone or in combination with proton, hydronium or hydroxide. Such additional mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, $Br^-$). Other mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In further embodiments, the aqueous electrolyte solutions described herein can also include one or more additional additives such as, but not limited to, a buffer, a supporting electrolyte, a viscosity modifier, a wetting agent, or any combination thereof. Illustrative buffers can include, but are not limited to, salts of phosphates, borates, carbonates, silicates, tris(hydroxymethyl)aminomethane (tris), 4-(2-hydroxyethyl)-1-piperazineethanesulfonic acid (hepes), piperazine-N,N'-bis(ethanesulfonic acid) (pipes), or any combination thereof. Other examples of suitable buffers and the other additional additives will be familiar to one having ordinary skill in the art.

In some embodiments, the aqueous electrolyte solutions of the present disclosure can have a concentration of the titanium catecholate complex of at least about 0.5 M, more particularly a concentration ranging between 0.5 M and about 3 M. In more particular embodiments, an aqueous electrolyte solution of the present disclosure can have a concentration of the titanium catecholate complex in the aqueous solution that ranges between 0.5 M and about 3 M. In other various embodiments, a concentration of the titanium catecholate complex in the aqueous electrolyte solution can be up to about 0.5 M, or up to about 1 M, or up to about 1.5 M, or up to about 2 M, or up to about 2.5 M, or up to about 3 M, particularly in an aqueous electrolyte solution. In more specific embodiments, a concentration of the titanium catecholate complex in the aqueous electrolyte solution can range between about 0.5 M and about 3 M, or between about 1 M and about 3 M, or between about 1.5 M and about 3 M, or between 1 M and about 2.5 M. In other more specific embodiments, a concentration of the titanium catecholate complex can range between about 1 M and about 1.8 M in an aqueous electrolyte solution.

In some embodiments, the aqueous electrolyte solutions of the present disclosure can provide high open circuit voltages within a flow battery. For example, the open circuit voltage can be at least about 0.8 V, or at least about 0.9 V, or at least about 1.0 V, or at least about 1.1 V, or at least about 1.2 V, or at least about 1.3 V, or at least about 1.4 V, or at least about 1.5 V, or at least about 1.6 V, or at least about 1.7 V, or at least about 1.8 V, or at least about 1.9 V, or at least about 2.0 V.

Illustrative flow batteries that can incorporate the foregoing titanium catecholate complex and aqueous electrolyte solutions will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like and any combination thereof.

Further, it is to be appreciated that while the disclosure herein is generally directed to flow batteries, other electrochemical energy storage media can incorporate the electrolyte solutions described herein, specifically those utilizing stationary electrolytes.

In some embodiments, flow batteries of the present disclosure can include: a first chamber containing a negative electrode contacting a first aqueous electrolyte; a second chamber containing a positive electrode contacting a second aqueous electrolyte, and a separator disposed between the first and second electrolytes. The electrolyte chambers provide separate reservoirs within the cell, through which the first and/or second electrolytes circulate so as to contact the respective electrodes and the separator. Each chamber and its associated electrode and electrolyte define a corresponding half-cell. The separator provides several functions which include, for example, (1) serving as a barrier to mixing of the first and second electrolytes, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle; electrolyte solutions can be transported from separate storage tanks through the corresponding electrolyte chambers. In a charging cycle, electrical power can be applied to the cell such that the active material contained in the second electrolyte undergoes a one or more electron oxidation and the active material in the first electrolyte undergoes a one or more electron reduction. Similarly, in a discharge cycle the second electrolyte is reduced and the first electrolyte is oxidized to generate electrical power.

In more specific embodiments, illustrative flow batteries of the present disclosure can include: (a) a first aqueous electrolyte containing a first coordination compound; (b) second aqueous electrolyte containing a second coordination compound; (c) a separator positioned between said first and second aqueous electrolytes; and (d) a mobile ion in the first and second aqueous electrolytes. As described in more detail below, the separator can be an ionomer membrane, and it can have a thickness of less than 100 microns and have an associated net charge that is the same sign as that of the first and second coordination compounds. In some embodiments, at least one of the first and second coordination compounds can include a catecholate ligand or a substituted catecholate ligand, as described hereinabove. In other various embodiments, one of the first and second coordination compounds can be a redox couple of ferricyanide [$Fe(CN)_6^{3-}$] and ferrocyanide [$Fe(CN)_6^{4-}$]. In more specific embodiments, the ferricyanide/ferrocyanide redox couple can be used as a first coordination compound and the second coordination compound can be a coordination compound containing a substituted catecholate ligand, particularly a titanium catecholate complex.

FIG. 1 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30, which is capable of being cycled between an oxidized and reduced state. For example, first active material 30 can be a titanium catecholate complex.

Pump 60 affects transport of first active material 30 from tank 50 to the electrochemical cell. The flow battery also suitably includes second tank 50' that contains second active material 40. Second active material 40 can be the same material as the first active material 30, or it can be different. For example, second active material 40 can be ferricyanide/ferrocyanide, as described above. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

As used herein, the terms "separator" and "membrane" refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to a polymer membranes containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in au ionomer can include anionic functional groups such as sulfate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—$CF$=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer, and inorganic filler, and open porosity. Suitable polymers can include, for example, high density polyethylene, polypropylene, polyvinyl idene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depends on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination compound, the average diameter of the coordination compound can be about 50% greater than the average pore size of the porous membrane. On the other hand, if a porous membrane has substantially uniform pore sizes, the average diameter of the coordination compound can be about 20% larger than the average pore size of the porous membrane. Likewise, the average diameter of a coordination compound is increased when it is further coordinated with at least one water molecule. The diameter of a coordination compound of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, less than about 300 micrometers, less than about 250 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, or less than about 10 micrometers. Suitable separators can include those in which the flow battery is capable of operating with a current efficiency of greater than about 85% with a current density of 100 Ma/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 Ma/cm$^2$. In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10^{-5}$ mol cm$^{-2}$ day$^{-1}$, less than about $1\times10^{-6}$ cm$^{-2}$ day$^{-1}$, less than about $1\times10^{-2}$ mol cm$^{-2}$ day$^{-1}$, less than about $1\times10^{-9}$ mol cm$^{-2}$ day$^{-1}$, less than about $1\times10^{-11}$ mol cm$^{-2}$ day$^{-1}$, less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). The matching charges of the first and/or second active materials and the ionomer membrane can provide a high selectivity. More specifically, charge matching can provide less than about 3%, less than about 2%, less than about 1%, less than about 0.5%, less than about 02%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where, the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 μm, less than about 75 less than about 50 μm, or less than about 250 μm; (f) where the flow battery is capable of operating at a current density of greater than about 100 mA/cm$^2$ with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad (1)$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad (2)$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \quad (3)$$

where [active material] and N are as defined above.

As used herein, the term "current density" will refer to the total current passed in an electrochemical cell divided by the geometric area of the electrodes of the cell and is commonly reported in units of mA/cm$^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{EFF,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

A titanium catecholate complex was prepared by reacting titanium tetrachloride and water under the conditions described in U.S. Pat. No. 3,425,796 to form an aqueous solution of titanium oxychloride. Three equivalents of catechol were added to the aqueous solution, and the pH was adjusted to 3 with equimolar portions of NaOH and KOH. Over time, the protonated form of the titanium tris(catecholate) complex precipitated from the aqueous solution. After isolation of the solid, the pH was then raised to 11 with equimolar portions of NaOH and KOH in H$_2$O, and the mixed Na$^+$/K$^+$ form of the titanium tris(catecholate) complex was obtained in an alkaline solution.

Figure 2:
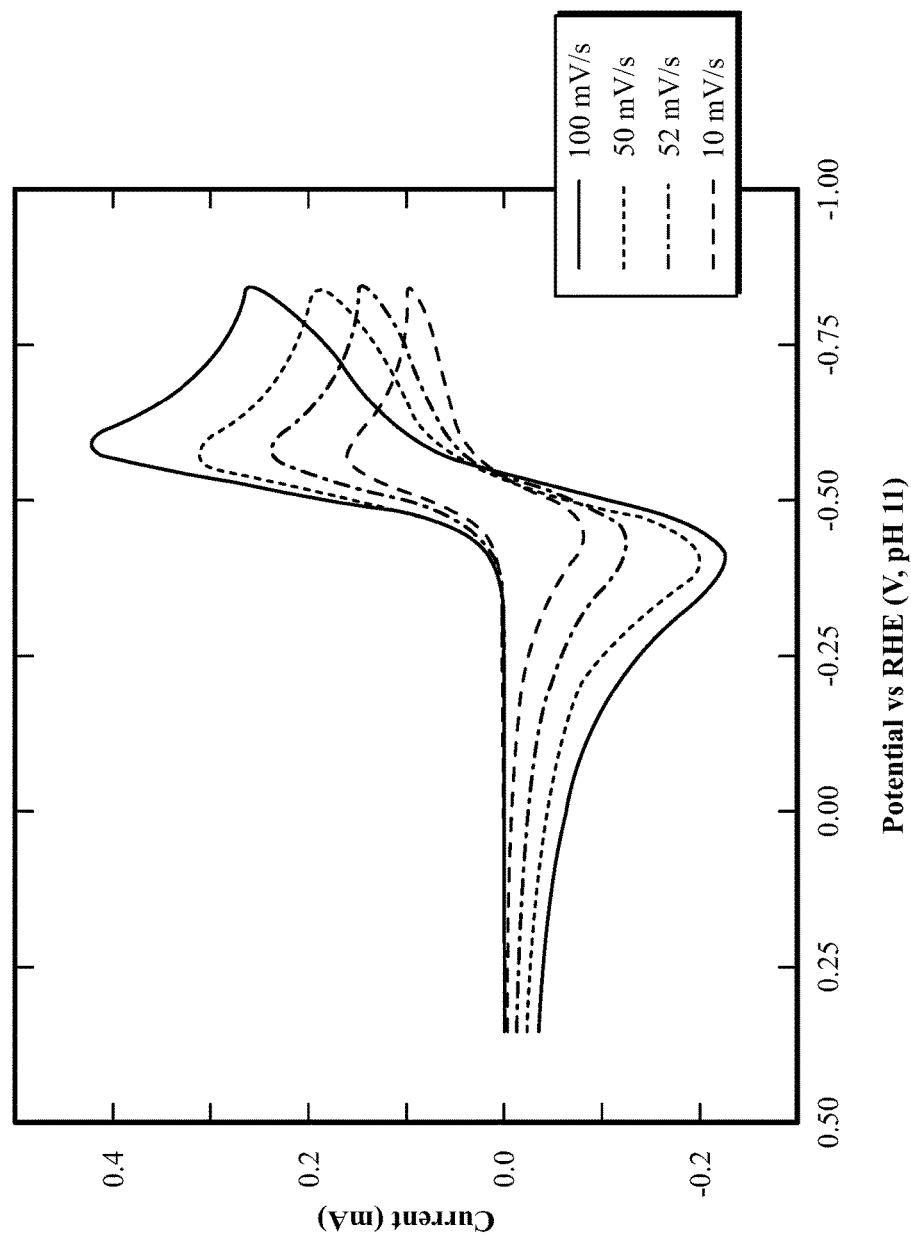
FIG. 2 shows an illustrative cyclic voltammogram of a 0.1 M solution of $Na^+/K^+Ti(catecholate)_3$ at various scan rates, where the complex was prepared using $TiOCl_2$ that was generated in situ.

FIG. 2 shows an illustrative cyclic voltammogram of a 0.1 M solution of Na$^+$/K$^+$Ti(catecholate)$_3$ at various scan rates, where the complex was prepared using TiOCl$_2$ that was generated in situ. The cyclic voltammograms were generated using a glassy carbon disc working electrode, a Pt wire counter electrode, and an Ag/AgCl reference electrode. The electrolyte solution also contained 0.1 M $Na_2SO_4$ and was buffered with 5 mM phosphate at a pH of 11. A reversible oxidation-reduction occurred at −0.51 V vs. RHE, which was consistent with that obtained from complexes prepared by other methods.

Figure 3:
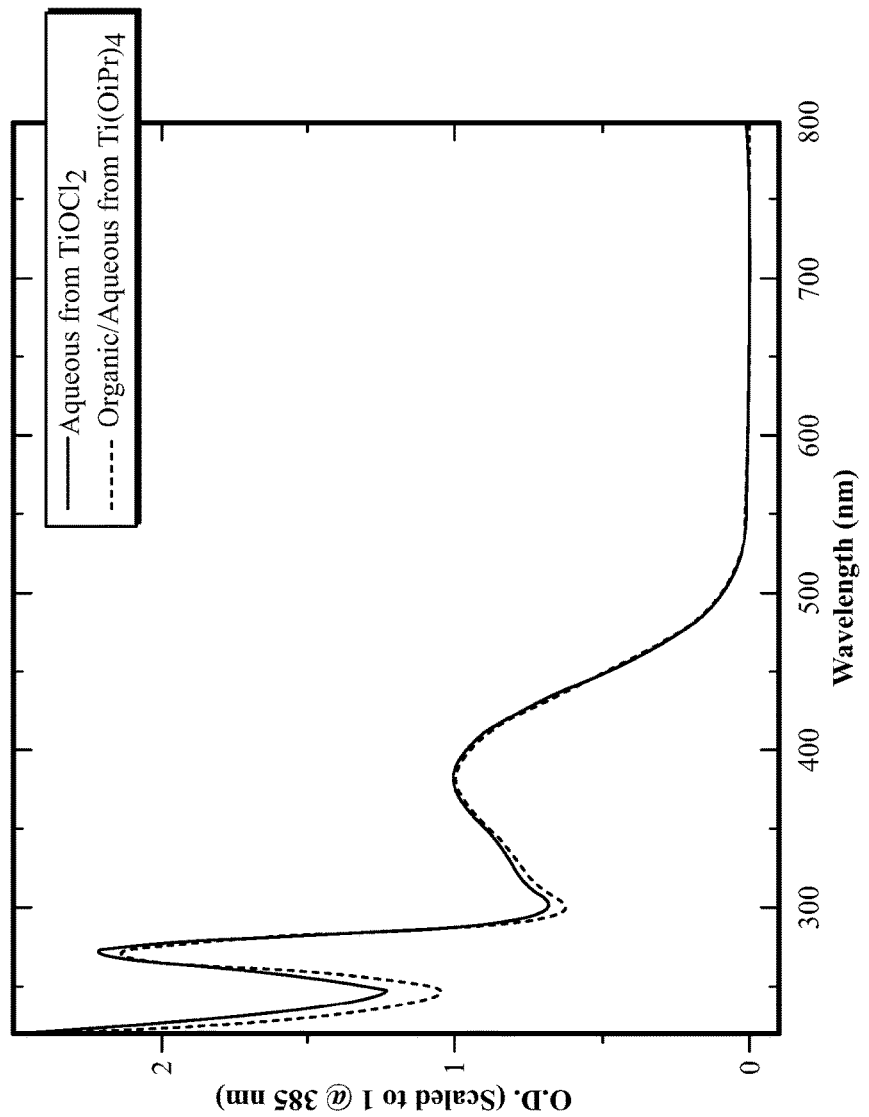
FIG. 3 shows an illustrative UV/VIS spectrum of a $Na^+/K^+Ti(catecholate)_3$ solution, where the complex was prepared using $TiOCl_2$ that was generated in situ, in comparison to that obtained in an organic solution using titanium tetrakis(isopropoxide).

FIG. 3 shows an illustrative UV/VIS spectrum of a $Na^+/K^+Ti(catecholate)_3$ solution, where the complex was prepared using $TiOCl_2$ that was generated in situ, in comparison to that obtained in an organic solution using titanium tetrakis(isopropoxide). The spectra for the two samples were nearly identical, except for slight differences in the 220-350 nm region. It is believed that these differences arise due to a minor catechol impurity in the titanium oxychloride preparation method.

Although the disclosure has been described with reference to the disclosed embodiments, those skilled in the art will readily appreciate that these only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
reacting one or more catecholate ligands with titanium oxychloride in an aqueous solution to form a titanium catecholate complex.

2. The method of claim 1, further comprising:
reacting the titanium catecholate complex with an aqueous base to form a salt of the titanium catecholate complex having a formula of:

$D_2Ti(L_1)(L_2)(L_3)$;

wherein:
D is $NH_4^+$, $NR_4^+$, $Li^+$, $Na^+$, $K^+$, or any combination thereof, where R is alkyl; and
$L_1$, $L_2$ and $L_3$ are ligands, at least one of $L_1$, $L_2$ and $L_3$ being a catecholate ligand or a substituted catecholate ligand.

3. The method of claim 1, wherein the substituted catecholate ligand contains a hydroxy group in the 3- or 4-position.

4. The method of claim 1, wherein the aqueous solution has a pH in a range of from 2.5 to 7.

5. The method of claim 4, wherein the titanium catecholate complex is isolated from the aqueous solution as a solid.

6. The method of claim 1, wherein the titanium catecholate complex has a formula of:

$H_2Ti(L_1)(L_2)(L_3)$;

wherein:
$L_1$, $L_2$ and $L_3$ are ligands, at least one of $L_1$, $L_2$ and $L_3$ being a catecholate ligand or a substituted catecholate ligand.

7. The method of claim 6, wherein each of $L_1$, $L_2$ and $L_3$ are a catecholate ligand or a substituted catecholate ligand.

8. The method of claim 6, wherein the titanium catecholate complex is isolated from the aqueous solution as a solid.

9. The method of claim 6, further comprising:
reacting the titanium catecholate complex with an aqueous base to form a salt of the titanium catecholate complex having a formula of:

$D_2Ti(L_1)(L_2)(L_3)$;

wherein:
D is $NH_4^+$, $NR_4^+$, $Li^+$, $Na^+$, $K^+$, or any combination thereof, where R is alkyl.

10. The method of claim 1, wherein at least a portion of the one or more catecholate ligands comprise a substituted catecholate ligand.

11. The method of claim 10, wherein the substituted catecholate ligand has a structure of:

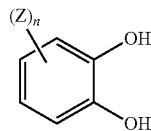

in a neutral form or a salt form, wherein:
n is an integer in a range of from 1 to 4, such that one or more Z are bound to the substituted catecholate ligand at an open aromatic ring position, each Z being the same or different when more than one Z is present; and
Z is a heteroatom functional group selected from the group consisting of $A^1R^{41}$, $A^2R^{42}$, $A^3R^{43}$, and CHO, wherein:
$A^1$ is $—(CH_2)_a—$ or $—(CHOR)(CH_2)_a—$, $R^{41}$ is $—OR^1$ or $—(OCH_2CH_2O)_bR^1$, a is 0, 1, 2, 3, 4, 5, or 6, with the proviso that $R^1$ is not H when a is 0 and $R^{41}$ is $—OR^1$, and b is an integer in a range of from 1 to 10, wherein:
R is H, $C_1$-$C_6$ alkyl, heteroatom-substituted $C_1$-$C_6$ alkyl, or $C_1$-$C_6$ carboxyalkyl; and
$R^1$ is H, methyl, ethyl, a $C_2$-$C_6$ polyol bound through an ether linkage or an ester linkage, or $C_1$-$C_6$ carboxyalkyl;
$A^2$ is $—(CH_2)_c—$ or $—CH(OR^2)(CH_2)_d—$, $R^{42}$ is $—NR^3R^4$, a carbon-linked amino acid, or $—C(=O)XR^5$, X is $—O—$ or $—NR^6—$, c is 0, 1, 2, 3, 4, 5, or 6, and d is 0, 1, 2, 3, or 4, wherein:
$R^2$, $R^3$, $R^4$ and $R^6$ are independently selected from the group consisting of H, $C_1$-$C_6$ alkyl, and heteroatom-substituted $C_1$-$C_6$ alkyl; and
$R^5$ is H, $C_1$-$C_6$alkyl, heteroatom-substituted $C_1$-$C_6$alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or $—(CH_2CH_2O)_bR^1$; and
$A^3$ is $—O—$ or $—NR^2—$, $R^{43}$ is $—(CHR^7)_eOR^1$, $—(CHR^7)_eNR^3R^4$, $—(CHR^7)_eC(=O)XR^5$, or $—C(=O)(CHR^7)_fR^8$, e is an integer in a range of from 1 to 6, with the proviso that e is not 1 when $A^3$ is $—O—$, and f is 0, 1, 2, 3, 4, 5, or 6, wherein:
$R^7$ is H or OH; and
$R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —$(OCH_2CH_2O)_bR^1$.

12. The method of claim 10, wherein the titanium catecholate complex has a formula of:

$$D_2Ti(L_1)(L_2)(L_3);$$

wherein:
D is H, $NH_4^+$, $NR_4^+$, $Li^+$, $Na^+$, $K^+$, or any combination thereof, where R is alkyl; and
$L_1$, $L_2$ and $L_3$ are ligands, at least one of $L_1$, $L_2$ and $L_3$ being a substituted catecholate ligand.

13. The method of claim 12, wherein each of $L_1$, $L_2$ and $L_3$ are a catecholate ligand or a substituted catecholate ligand.

14. The method of claim 1, further comprising:
combining titanium tetrachloride with water at conditions under which the titanium tetrachloride reacts with the water to form the titanium oxychloride; and
optionally diluting the titanium oxychloride to form the aqueous solution.

15. The method of claim 14, wherein the titanium tetrachloride reacts with the water at a temperature in a range of from −10° C. to −40° C.

16. The method of claim 14, wherein the one or more catecholate ligands are combined with the aqueous solution after the titanium oxychloride has been formed.

17. The method of claim 14, wherein the conditions under which the titanium tetrachloride reacts with the water are such that titanium dioxide is not formed.

18. The method of claim 14, wherein the aqueous solution has a pH in a range of from 2.5 to 7.

19. The method of claim 14, wherein the titanium tetrachloride reacts with the water at a temperature below about 0° C.

20. The method of claim 19, wherein the water is added to the titanium tetrachloride as ice and the titanium tetrachloride is also in a solid form.

* * * * *